United States Patent [19]

Poot et al.

[11] 3,958,815
[45] May 25, 1976

[54] PRESSURE-SENSITIVE RECORDING MATERIALS

[75] Inventors: Albert Lucien Poot, Kontich; Raymond Gerard Lemahieu, Mortsel; Wilhelmus Janssens, Aarschot; Antoine August de Jaeger, Wilrijk, all of Belgium

[73] Assignee: AGFA-GEVAERT N.V., Mortsel, Belgium

[22] Filed: Dec. 27, 1973

[21] Appl. No.: 428,687

[30] Foreign Application Priority Data
Dec. 28, 1972 United Kingdom............... 59843/72
Apr. 11, 1973 United Kingdom............... 17403/73

[52] U.S. Cl. ........................... 282/27.5; 260/240 F; 260/240 R; 260/246 B; 260/247; 260/247.1 M; 260/247.1 P; 260/293.51; 260/293.71; 260/319.1; 260/326.2; 260/611 A; 260/329 AM; 260/329 R; 260/333; 428/411

[51] Int. Cl.²..................... B41M 5/10; B41M 5/14; B41M 5/22

[58] Field of Search............... 8/90 R; 117/1.7, 36.2, 117/36.7, 36.8, 36.9; 96/48, 90 R; 260/240 R, 240 K, 293, 240.1, 240.6, 240.65, 247.1, 611 A, 246 B, 326.11, 326.12, 319.1, 326.15

[56] References Cited
UNITED STATES PATENTS

| | | | |
|---|---|---|---|
| 2,505,475 | 4/1950 | Green | 117/36.9 |
| 2,505,484 | 4/1950 | Green | 117/36.9 |
| 2,929,736 | 3/1960 | Miller et al. | 117/36.9 |
| 3,140,947 | 7/1964 | Foris | 96/48 |
| 3,287,154 | 11/1966 | Haas | 117/36.9 |
| 3,310,401 | 3/1967 | Greig | 96/1.5 |
| 3,489,568 | 1/1970 | Hackmann et al. | 96/90 |
| 3,527,517 | 9/1970 | Hackmann | 96/90 |
| 3,536,517 | 10/1970 | Van den Heuvel et al. | 117/36.2 |
| 3,544,557 | 12/1970 | Nauta | 260/239 |
| 3,637,675 | 1/1972 | Brust et al. | 260/240 F |
| 3,637,748 | 1/1972 | Psaar et al. | 260/326.15 |
| 3,684,510 | 8/1972 | Psaar et al. | 96/48 R |
| 3,752,825 | 8/1973 | Raue et al. | 260/326.11 |
| 3,828,071 | 8/1974 | Kast et al. | 260/326.15 |
| 3,850,913 | 11/1974 | Psaar | 260/240.8 |

FOREIGN PATENTS OR APPLICATIONS

| | | |
|---|---|---|
| 931,885 | 7/1963 | United Kingdom |
| 1,042,596 | 9/1966 | United Kingdom |
| 1,281,492 | 7/1972 | United Kingdom |
| 482,224 | 1/1970 | Switzerland |

*Primary Examiner*—P. E. Willis, Jr.
*Attorney, Agent, or Firm*—William J. Daniel

[57] ABSTRACT

A pressure-recording process in which a methine dye is produced by bringing image-wise into reactive contact with the aid of pressure, a compound reacting as an acid with a dye precursor compound corresponding to the following general formula:

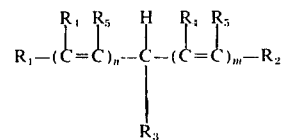

wherein:
$R_1$ represents (1) an aryl group substituted with an ether group $R_6$—O— in which $R_6$ represents a hydrocarbon group or (2) a heterocyclic group;
$R_2$ represents (1) an aryl group substituted with an ether group $R_6$—O— in which $R_6$ represents a hydrocarbon group, (2) a heterocylic group or (3) a

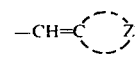

group, in which Z represents the necessary atoms to close a heterocylic nucleus,
$R_3$ represents (1) a —XH or —X—$R_7$ group, in which X is oxygen or sulfur, and $R_7$ is an organic group, (2) a

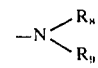

group in which each of $R_8$ and $R_9$ (same or different) represents hydrogen or an alkyl group, a cycloalkyl group, an aralkyl group, or an aryl group, or $R_8$ and $R_9$ together represent the necessary atoms to close a nitrogen-containing heterocyclic nucleus, or (3) a

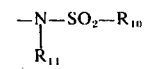

group
in which $R_{10}$ represents an alkyl group or a cycloalkyly group, an aralkyl group, an aryl group or a heterocyclic group and $R_{11}$ represents hydrogen or a group emumerated in the definition of $R_{10}$, or $R_{11}$ and $R_{10}$ together represent sultam group,
each of $R_4$ and $R_5$ (same or different) represents hydrogen, a $C_1$ - $C_5$ alkyl group, a cycloalkyl group, an aralkyl group or an aryl group,
$n$ is 0 or 1, and
$m$ is 0 or 1.

19 Claims, No Drawings

PRESSURE-SENSITIVE RECORDING MATERIALS

The present invention relates to pressure-sensitive materials suited for the recording and/or reproduction of information and to any "pressure-activatable image-forming process" using such materials.

By a "pressure-activatable image-forming process" there is meant that a visible image is produced by pressure applied in the form of "information". The information may be in the form of pressure signals applied in successive order e.g. as in the writing with a stylus or with the keys of a typewriter. The information can also be applied simultaneously e.g. by pressing a letterpress printing block onto the pressure-sensitive material.

The recording materials of the present invention can be divided into two groups viz. (1) single-sheet materials and (2) sets of sheet materials incorporating different chemical compounds, which in the pressure-struck area can enter into reaction with each other and provide a visible change of colour therein.

In both said types of sheet materials use is made of reactants that are capable of producing a dyestuff and that are shielded from premature chemical contact by a pressure-rupturable film-forming envelope.

In the mono-sheet system different techniques of shielding a first reactant and a second reactant e.g. a dye precursor compound from the reactive chemical contact with each other can be used. For example, the reactants are shielded from direct chemical contact by enveloping at least one of them in a capsule that contains a sheel or envelope of a material, normally a polymeric material, or by incorporating at least one of them in a droplet of oil or wax that prevents the direct contact with the other reactant. The capsule shell or droplet is ruptured by pressure so that the reactants come into reactive contact.

The capsules or droplets containing a first reactant can be dispersed in the paper mass of a paper sheet or in a binder or binder system containing the second reactant in dispersed or dissolved form. Such type of single-sheet pressure-sensitive material has been described e.g. in the United Kingdom 1,042,596 filed Jan. 29, 1963 by Minesota Mining & Manufacturing Company.

The inner part of the capsule may be of organic water-immiscible nature and the sheel or envelope may contain or consist of a hydrophilic material e.g. a hydrophilic polymer or a colloid that is hardened optionally. Capsules of this type have been described e.g. in the United Kingdom Patents 1,281,492 filed Apr. 19, 1971 by Nat. Cash Register, 1,276,598 filed Aug. 3, 1970 by Fuji Photo Film and 1,034,437 filed Feb. 20, 1963 by Gevaert Photo-Production N.V.

According to another embodiment the content of the capsule is hydrophilic. For example the capsule contains a first reactant dissolved or dispersed in water. The material of the capsule shell is not soluble in water. The preparation of the latter type of capsules has been described in the United Kingdom Patents 1,048,696 and 1,048,697 both filed July 10, 1963 by Gevaert Photo-Production N.V. and 1,298,194 filed Nov. 20, 1968 by Gevaert-Agfa N.V. and in the Belgian Patent 792,550 filed Dec. 11, 1972 by Agfa-Gevaert N.V.

Yet it is not necessary to shield the reactants from contact in capsules. Thus, e.g. in the U.S. Patent 2,505,471 of Barrett K. Green issued Apr. 25, 1950 a process has been described for the production of a single-sheet pressure-sensitive recording material that does not contain microcapsules, but in which a film-like deposit is formed of solid particles of a plurality of color-forming reactants disposed in contiguity with each other and a solid insulating medium derived from an organic film-forming hydrophilic colloid substance insulating said reactant particles from color-forming reaction with each other. At least one of said reactants is an inorganic compound and at least another of said reactants is an organic compound. The reactants are selected so as to react in the absence of a liquid ionizing medium for the reactants to form a distinctive color when brought in contact with each other. The inorganic reactant is in fine particle form, provides a large adsorbent surface area, and is an acid relative to the organic reactant so as to be an electron-acceptor when brought in adsorptive contact with said organic reactant.

Another example of a capsule-free pressure-sensitive single-sheet recording material has been described in the Belgian Patent 768,952 filed June 24, 1971 by G. Wagner Pelikan Werke. According to the invention described therein an acid-sensitive spiro-dipyran compound acting as dye precursor compound is applied to a support in a first hydrophilic binder layer and said first layer is coated with a second layer containing acid-treated clay in another hydrophilic binder shielding the acid clay from direct chemical contact with the spiro-dipyran compound. Pressure brings the reactants together and results in a coloured image or image marking in correspondence with the pattern of the pressure applied.

A multiple-sheet pressure-sensitve recording material pack usually contains one reactant coated on the rear side of a first sheet that is writable on the front side. The corresponding co-reactant is provided on the front side of a further sheet in contact with the first sheet, said sheets being separatable from each other and containing the reactants in such condition that the contact of the sheets in the absence of pressure does not allow the formation of colour.

Such multiple-sheet materials may consist of three different types of coated paper in a manifold paper pack. The top sheet, called the CB-pape (coated back) has a colouring coating at the rear side; the intermediate sheet or CFB-paper (coated front and back) has a receiving chemical coating on its front side and the former colouring coating at the rear side. The third sheet or CF-paper (coated front) contains the receiving chemical at the front side, but has not coating at the rear side. The impact of a typewriter key or the pressure of a pencil on the first sheet presses the chemical on the CB-paper into contact with the chemical coating at the front side of the CFB-paper and the paper reaction produces a coloured print. The chemical of the transferable colouring coating at the rear side of the CFB-baper is transferred by pressure to the co-reactant(s) of the CF-paper. Paper of this type can be applied in account listings, tabulator forms, teletype rolls, adding-machine rolls, note blocks, etc.

It is an object of the present invention to provide improved pressure-sensitive recording sheets. Said sheets may be of the single-sheet type or of the multiple-sheet type, a so-called manifold pack.

The present invention more particularly includes the use in a pressure-recording process of a colour reaction produced by allowing to react an acid-sensitive dye precursor compound with an acid-reacting compound, said dye precursor compound corresponding to the following general formula:

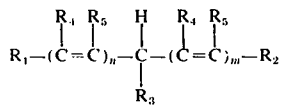

wherein:
R₁ represents (1) a substituted aryl group e.g. a substituted phenyl, tolyl, xylyl, naphthyl, biphenyl, or indenyl group at least one substituent of said aryl group being an ether group $R_6$—O— in which $R_6$ represents an organic group e.g. an alkyl group including a substituted alkyl group, e.g. a methyl, ethyl, propyl, hexyl, dodecyl, or octadecyl group, a cycloalkyl group including a substituted cycloalkyl group e.g. a cyclopentyl, cyclohexyl, or methylcyclohexyl group, an aralkyl group including a substituted aralkyl group e.g. a benzyl or phenethyl group, an aryl group including a substituted aryl group e.g. a phenyl group or tolyl group or (2) a heterocyclic group including a substituted heterocyclic group e.g. an indolyl, pyrryl, thienyl, furyl, carbazolyl or indolizinyl group, R₂ represents a substituted aryl group e.g. a substituted phenyl, tolyl, xylyl, naphthyl, biphenyl or indenyl group, at least one substituent of said aryl group being an ether group $R_6$—O—, in which $R_6$ represents an organic group e.g. an alkyl group including a substituted alkyl group, e.g. a methyl, ethyl, propyl, hexyl, dodecyl, or octadecyl group, a cycloalkyl group including a substituted cycloalkyl group e.g. a cyclopentyl, cyclohexyl, or methylcyclohexyl group, an aralkyl group including a substituted aralkyl group e.g. a benzyl or phenethyl group, an aryl group including a substituted aryl group e.g. a phenyl group or tolyl group or a heterocyclic group including a substituted heterocyclic group e.g. an indolyl, pyrryl, thienyl, furyl, carbazolyl, or indolizinyl group, or a

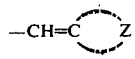

group in which Z represents the necessary atoms to close a heterocyclic nucleus including a substituted heterocyclic nucleus e.g. a nitrogen-containing heterocyclic nucleus, the indolylidene-(2) group being an example thereof, R₃ represents (1) a —XH or —X—R₇ group, in which X is oxygen or sulphur and R₇ is an organic group e.g. an alkyl group including a substituted alkyl group e.g. methyl, a cycloalkyl group including a substituted cycloalkyl group e.g. a cyclohexyl group, an aralkyl group including a substituted aralkyl group e.g. a benzyl group, an aryl group including a substituted aryl group e.g. a phenyl group, or an heterocyclic group including a substituted heterocyclic group, (2) a

group wherein each of $R_8$ and $R_9$ (same or different) represents hydrogen or an alkyl group e.g. a $C_1$–$C_5$ alkyl group, a cycloalkyl group, an aralkyl group, or an aryl group or $R_8$ and $R_9$ together represent the necessary atoms to close a nitrogen-containing heterocyclic nucleus e.g. a piperidine, pyrrolidine, or morpholine nucleus, or (3) a

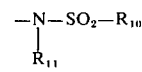

group in which $R_{10}$ represents an alkyl group including a substituted alkyl group e.g. methyl, propyl, hexyl, dodecyl, or octadecyl, or a cycloalkyl group including a substituted cycloalkyl group e.g. cyclopentyl, cyclohexyl, or methylcyclohexyl, an aralkyl group including a substituted aralkyl group e.g. benzyl or phenethyl, an aryl group including a substituted aryl group e.g. a phenyl, tolyl, xylyl, naphthyl, biphenyl or indenyl group, a heterocyclic group including a substituted heterocyclic group e.g. a pyridyl, quinolyl, benzothiazolyl, or phenothiazolyl group; the substituents being e.g. alkoxy, fluoro, chloro, bromo, dialkylamino, acylamino, or sulphamyl and in which $R_{11}$ represents hydrogen or represents a group enumerated in the definition of $R_{10}$, or $R_{11}$ and $R_{10}$ together represent a sultam group, each of $R_4$ and $R_5$ (same or different) represents hydrogen, a $C_1$–$C_5$ alkyl group, a cycloalkyl group, an aralkyl group e.g. benzyl or an aryl group e.g. a phenyl group, n is 0 or 1, and
m is 0 or 1.

The dye precursor compounds involved do not contain acid substituents.

Representatives of particularly suitable dye precursor compounds are given in the following table.

Table

-continued

| No. | Dye precursor compound | Melting point °C |
|---|---|---|
| 2 | (structure: bis(3,4,5-trimethoxyphenyl)methane with OCH$_3$ on central CH) | 150 |
| 3 | (indole linked via CH(OCH$_3$) to 3,4,5-trimethoxyphenyl) | 150 (decomp.) |
| 4 | (morpholino-substituted thiophene with diphenyl, CH(OH) linked to 3,4,5-trimethoxyphenyl) | 160 |
| 5 | (benzimidazole with 4-bromophenyl, CH(OCH$_3$) linked to 3,4,5-trimethoxyphenyl) | 100 (decomp.) |
| 6 | (morpholino-substituted diphenyl thiophene with CH(OH) linked to naphthyl-O-(CH$_2$)$_{15}$-CH$_3$) | 145 |
| 7 | (1-methylindole with phenyl, morpholino, CH linked to 3,4,5-trimethoxyphenyl) | 204 |

-continued

| No. | Dye precursor compound | Melting point °C |
|---|---|---|
| 8 | (structure: 2,4,5-trimethoxyphenyl-CH=CH-CH(morpholino)-2,4,5-trimethoxyphenyl) | 124 |
| 9 | (structure: 2-morpholino-4,5-diphenylthiophene-CH(OH)-3,4,5-trimethoxyphenyl) | 140 |
| 10 | (structure: 2-morpholino-4,5-diphenylthiophene-CH(OCH₃)-2,4,5-trimethoxyphenyl) | 161 |
| 11 | (structure: 2-morpholino-4,5-diphenylthiophene-CH(OCH₃)-9-ethylcarbazole) | 175 |
| 12 | (structure: bis(indol-2-yl)methoxymethane) | 150 |

Table -continued

| No. | Dye precursor compound | Melting point °C |
|---|---|---|
| 13 | (structure) | 70 (decomp.) |
| 14 | (structure) | 216 |
| 15 | (structure) | 140 (decomp) |
| 16 | (structure) | 192 |
| 17 | (structure) | 198 |

-continued

| No. | Dye precursor compound | Melting point °C |
|---|---|---|
| 18 | (structure) | 177 |
| 19 | (structure) | 135 |
| 20 | (structure) | 150 |
| 21 | (structure) | 176 |

-continued

| No. | Dye precursor compound | Melting point °C |
|---|---|---|
| 22 | (structure) | 125 |
| 23 | (structure) | 198 |
| 24 | (structure) | 150 |
| 25 | (structure) | 210 |
| 26 | (structure) | 100 (decomp.) |

-continued
| No. | Dye precursor compound | Melting point °C |
|---|---|---|
| 27 | 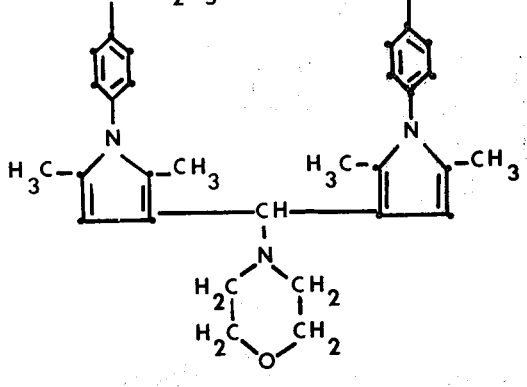 | 100 (decomp.) |
| 28 | 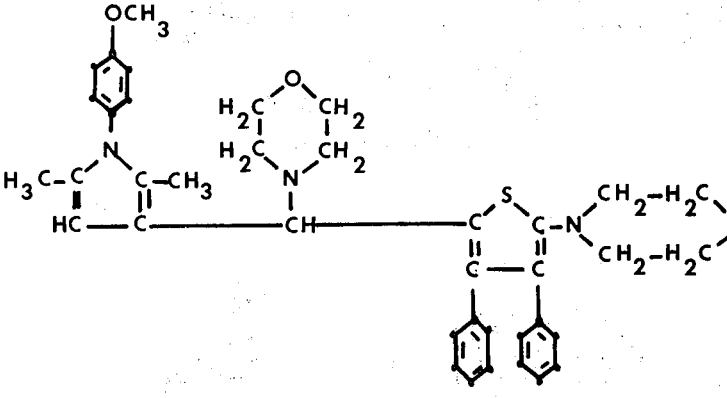 | 154 |
| 29 | 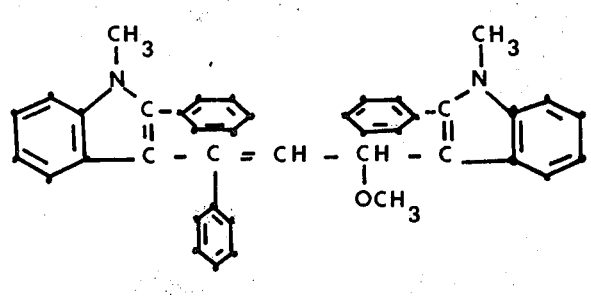 | 140 |
| 30 | 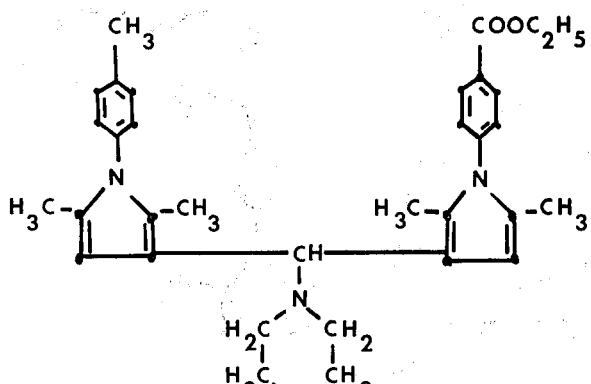 | 135 |

-continued

| No. | Dye precursor compound | Melting point °C |
|---|---|---|
| 31 | (structure) | 120 |
| 32 | (structure) | decomposition 140–150 |
| 33 | (structure) | 142 |
| 34 | (structure) | 134 |

-continued

| No. | Dye precursor compound | Melting point °C |
|---|---|---|
| 35 | (structure) | 150 |
| 36 | (structure) | 136 |
| 37 | (structure) | 100 |
| 38 | (structure) | 115 |

The preparation of the dye precursor compound is illustrated by the following detailed preparation receipts.

1. Preparation of dye precursor compound 1

At a temperature of 15°C 500 ml of ethanol saturated with hydrogen chloride gas were added dropwise to a solution of 168 g (1 mole) of 1,3,5-trimethoxybenzene and of 90 g. (0.55 mole) of malondialdehyde tetramethylacetal in 500 ml of dry ethanol. The dyestuff corresponding to the dye precursor compound crystallized in the reaction mixture. After separation the dyestuff was first washed with a mixture of ethanol and ether (1:9 by volume) and subsequently with ether alone.

Yield: 204 g.

1300 ml of a 10% by weight aqueous sodium carbonate solution were added with stirring to 120 g of the dyestuff dissolved in a mixture of 1000 ml of methylene chloride and 200 ml of methanol. The reaction mixture became colourless and the dye precursor compound (leuco base) dissolved into the organic liquid phase.

The organic phase was separated and dried with anhydrous potassium carbonate. Subsequently the solvent was distilled off. The leuco base was recrystallized from acetonitrile.

Yield: 59.7 g. Melting point: 160°C.

(The preparation of the dyestuff has been described already, see G. Zinner and R. Uhlig, Angew. Chem. (1961) No. 13, pgs. 467–468).

2. Preparation of dye precursor compound 2

At a temperature of 10°C 375 ml of ethanol saturated with hydrogen chloride were added dropwise to a solution of 42 g (0.25 mole) of 1,3,5-trimethoxybenzene and 49 g (0.25 mole) of 2,4,6-trimethoxybenzaldehyde. The dyestuff that crystallized in the reaction mixture was sucked off and washed first with a small amount of cold ethanol and afterwards with ether.

Yield: 55.2 g. Melting point: approximatively 140°C.

45.2 g of the obtained dyestuff were dissolved in a mixture of 450 ml of methylene chloride and of 45 ml of methanol and converted into the colourless leuco form by mixing it with a 675 ml of a 10% by weight aqueous solution of sodium carbonate. The leuco base passed into the organic phase. The solvent was evaporated. The residue left contained the leuco base.

Yield: 26 g. Melting point: 150°C.

3. Preparation of dye precursor compound 3

10 g of anhydrous zinc chloride were added to a mixture of 4.35 g (0.03 mole) of 3-formylindole and of 5.5 g (0.33 mole) of 1,3,5-trimethoxybenzene dissolved in 50 ml of acetic anhydride. The reaction mixture was stirred at room temperature (20°C) for 1 hour. The dyestuff that crystallized was sucked off and washed with water.

Yield: 8.9 g. Melting point: 210°C (decomposition).

8.5 g of the obtained dyestuff were dispersed in 100 ml of methylene chloride. 20 ml of methanol and 2.6 g of potassium hydroxide were added to the dispersion. The colourless methylene chloride solution obtained was washed with water and dried over anhydrous potassium carbonate. Finally the solvent was distilled off to leave the leuco base.

Yield: 5.8 g. Melting point: 150°C (decomposition).

4. Preparation of dye precursor compound 4

80 g (0.25 mole) of 2-morpholino-3,4-diphenylthiophene and 49 g (0.25 mole) of 3,4,5-trimethoxybenzaldehyde were dissolved with stirring in 625 ml of dry ethanol saturated with hydrogen chloride. After stirring of the reaction mixture for 1 hour the precipitated dyestuff was sucked off.

Yield: 114.5 g. Melting point: approximately 220°C.

4 g of the obtained dyestuff were dissolved in 40 ml of methylene chloride. The solution was discoloured by shaking with 60 ml of an aqueous 10% by weight sodium carbonate solution. The colourless methylene chloride solution was dried with anhydrous potassium carbonate and the solvent was distilled off to leave the carbinol base.

Yield: 3 g. Melting point: 160°C.

5. Preparation of dye precursor compound 5

At room temperature 5 g of anhydrous zinc chloride were added to a mixture of 5.1 g (0.017 mole) of 2-(p-bromophenyl-3-formylindole and of 2.9 g (0.017 mole) of 1,3,5-trimethoxybenzene dissolved in 50 ml of acetic anhydride. The reaction mixture was stirred for 1 hour at room temperature. The dyestuff that crystallized from the reaction mixture was sucked off and washed with water.

Yield: 7 g.

The dyestuff was dissolved in a mixture of 100 ml of methylene chloride and 20 ml of methanol. 3 g of potassium hydroxide were added thereto. Water was added to the solution obtained. Subsequently the organic phase was dried with anhydrous potassium carbonate. The solvent was distilled off to obtain the leuco base.

Yield: 5.1 g.

6. Preparation of dye precursor compound 6

10 g of anhydrous zinc chloride were added to a mixture of 6.4 g (0.02 mole) of 2-morpholine-3,4-diphenylthiophene and 8 g (0.02 mole) of 4-hexadecyloxy-naphthaldehyde dissolved in 100 ml of acetic anhydride. The reaction mixture was stirred for 1 hour at room temperature. Subsequently, the reaction mixture was poured on ice.

The sticky precipitate was treated with methanol and sodium perchlorate to form the crystalline perchlorate dye salt.

Methylene chloride and an aqueous ammonia solution were added to the perchlorate salt. The organic phase was dried with potassium carbonate and the solvent was evaporated.

Yield: 2.1 g of carbinol base.

7. Preparation of dye precursor compound 7

9.8 g (0.05 mole) of 2,4,6-trimethoxybenzaldehyde were added portion-wise to a solution of 10.35 g (0.05 mole) of 1-methyl-2-phenylindole in a mixture of 75 ml of ethanol and 75 ml of ethanol saturated with hydrogen chloride. During the addition of the benzaldehyde derivative the reaction mixture was stirred and kept at a temperature of 15°C by cooling.

After a reaction period of 2 hours a solution of 12.5 g of sodium perchlorate in 50 ml of methanol was added. The crystallized dyestuff was separated and recrystallized from ethanol.

Yield: 11 g. Melting point: 204°C.

To 5 g of the dyestuff dissolved in 50 ml of methylene chloride 2.5 ml of morpholine were added. After washing with water and drying with potassium carbonate the solvent was evaporated.

Yield of the dye precursor compound: 4.3 g. Melting point: 204°C.

8. Preparation of dye precursor compound 8

10 g of the dyestuff prepared as described in preparation 1 were dissolved in 100 ml of methylene chloride and allowed to react with 5 ml of morpholine. After evaporating the solvent the obtained solid was recrystallized from ethanol.

Yield of the dye precursor compound: 4 g. Melting point: 124°C.

9. Preparation of dye precursor compound 9

9.8 g (0.05 mole) of 2,4,6-trimethoxybenzaldehyde were added portion-wise to a solution of 16 g (0.05 mole) of 2-morpholino-3,4-diphenyl-thiophene in a mixture of 100 ml of ethanol and 100 ml of ethanol saturated with hydrogen chloride. During the addition of the benzaldehyde derivative the reaction mixture was stirred and kept at a temperature of 15°C.

The crystallized dyestuff was separated.

Yield: 19.1 g. Melting point: 120°C.

To 6 g of the dyestuff dissolved in 100 ml of methylene chloride 20 ml of a concentrated aqueous ammonia solution were added. The organic phase was separated, dried with potassium carbonate and the solvent evaporated.

Yield of the dye precursor compound: 5 g. Melting point: 140°C.

10. Preparation of dye precursor compound 10

To 80 g of the dyestuff prepared as described in preparation 4 and dissolved in 400 ml of methanol 50 ml of triethylamine were added. The formed dye precursor compound was separated and washed with water and methanol.

Yield: 56.2 g. Melting point: 161°C.

11. Preparation of dye precursor compound 11

84 ml of concentrated sulphuric acid were added dropwise to 500 ml of methanol while cooling the mixture. 124 g (0.36 mole) of 2-morpholino-3,4-diphenyl-thiophene were added to the mixture obtained. 80.4 g of N-ethyl-3-formylcarbazole dissolved in 750 ml of methanol were added dropwise with thorough stirring to the solution obtained at a temperature between 10° and 15°C over a period of 2 hours. The reaction mixture was kept at room temperature for a further 2 hours, thereupon cooled down, whereafter the crystals obtained were sucked off. The resulting precipitate was washed three times with 400 ml of water.

Yield of dyestuff: 194 g. Melting point: 236°C.

150 g of the obtained dyestuff were dispersed into a mixture of 500 ml of methylene chloride and of 50 ml of methanol. 250 g of aqueous ammonia were added to the mixture with cooling. The organic phase was separated and dried with anhydrous potassium carbonate. The solvent was evaporated and the residue digested in benzin.

Yield of the leuco base: 130 g. Melting point: 175°C.

12. Preparation of dye precursor compound 12

13.6 g of anhydrous zinc chloride were added to a mixture of 5.9 g (0.05 mole) of indole and 8.7 g (0.05 mole) of 3-formylindole dissolved in 100 ml of acetic anhydride. The reaction mixture was kept at room temperature for 1 hour, thereupon cooled down and the dye crystals formed were sucked off, washed with water, and dried.

Yield: 9.2 g.

9 g of the dyestuff obtained were dissolved in a mixture of 100 ml of methylene chloride and 20 ml of methanol and treated with 20 ml of an aqueous concentrated ammonia solution. After drying of the organic phase with anhydrous potassium carbonate the solvent was evaporated and the colourless leuco base was obtained.

Yield: 6.5 g.

Melting point: 150°C.

13. Preparation of dye precursor compound 13

13.6 g of anhydrous zinc chloride were added to a mixture of 11.75 g (0.05 mole) of 1-octyl-2,5-dimethyl-3-formylpyrrole and of 10.35 (0.05 mole) of 1-methyl-2-phenylindole dissolved in 50 ml of acetic anhydride. The reaction mixture was kept for 1 hour at 20°C. Subsequently the mixture was poured into 200 ml of water containing 20 g of sodium perchlorate. The crystalline dyestuff obtained was sucked off and washed with water.

Yield: 25.6 g.

8 g of this dyestuff were dissolved in 50 ml of methylene chloride and treated with 10 ml of a 10% by weight aqueous potassium hydroxide solution. The organaic phase was dried on anhydrous potassium carbonate, the solvent was evaporated and the colourless carbinol base was obtained.

Yield: 6 g.

Melting point: approximately 70°C (decomposition).

14. Preparation of dye precursor compound 14

13.6 g of anhydrous zinc chloride were added to a mixture of 10.4 g (0.05 mole) of 1-methyl-2-phenylindole and 11.8 g (0.05 mole) of 1-methyl-2-phenyl-3-formyl indole dissolved in 100 ml of acetic anhydride. The reaction mixture was kept at 20°C for 2 hours. Subsequently the reaction mixture was poured into a solution of 20 g of sodium perchlorate in 100 ml of methanol. The dyestuff formed was sucked off and recrystallized from methanol.

Yield: 15.9 g. Melting point: 250°C.

8 g of the dyestuff were dissolved in 100 ml of a mixture of methylene chloride and 20 ml of methanol and treated with 30 ml of a 10% by weight solution of potassium hydroxide. The liquid organic phase was separated and dried over anhydrous potassium carbonate. After evaporation of the solvent and washing of the residue with benzin, 3.2 g of dye precursor compound were obtained.

Melting point: 216°C.

15. Preparation of dye precursor compound 15

2.2 ml of an aqueous concentrated hydrogen bromide solution were added to a mixture of 4.12 g (0.02 mole) of 1-methyl-2-phenylindole and of 1.64 g (0.01 mole) of malonaldehyde tetramethylacetal in 25 ml of ethanol. The reaction mixture was heated to boiling temperature and cooled down by pouring it into iced water. The dyestuff crystallized and was sucked off and washed with benzene and ether. The dyestuff was recrystallized from methanol.

Yield: 3.6 g. Melting point: 250°C.

2.5 g of the dyestuff were dissolved in 50 ml of methylene chloride and treated with 10 ml of a 10% by weight aqueous solution of potassium hydroxide.

The organic phase was dried with anhydrous potassium carbonate and afterwards the solvent was evaporated. 2 g of carbinol base were obtained.

Melting point: 140°C (decomposition).

16. Preparation of dye precursor compound 16

17.5 g (0.05 mole) of 2-morpholino-3,4-diphenyl-5-formyl-thiophene were added portion-wise to a solution of 11.6 g (0.05 mole) of 1-(3,4-dimethoxyphenyl)-2,5-dimethylpyrrole in a mixture of 75 ml of ethanol and 75 ml of ethanol saturated with hydrogen chloride. During the addition of the thiophene derivative the reaction mixture was stirred and kept at a temperature of 15°C.

After a reaction period of 2 hours a solution of 12.5 g of sodium perchlorate in 50 ml of methanol was added. The crystallized dyestuff was separated.

Yield : 28.2 g. Melting point : 230°C.

6 g of the obtained dyestuff were dissolved in 100 ml of methylene chloride and allowed to react with 5 ml of morpholine. After evaporating the solvent the dye precursor compound was recrystallized from ethanol.

Yield : 5.6 g. Melting point : 192°C.

17. Preparation of dye precursor compound 17

The preparation of said compound proceeded analogously to the preparation of compound 16.

Melting point : 198°C.

18. Preparation of dye precursor compound 18

6.1 g (0.032 mole) of malondialdehyde tetramethyl acetal dissolved in 75 ml of ethanol were added at room temperature to 20 g (0.074 mole) of 1,2-diphenylindolizine dissolved in 50 ml of ethanol saturated with hydrogen chloride. The reaction mixture was heated to boiling temperature and maintained at that temperature for 90 min. The dyestuff crystallized and was separated from the cooled mixture. Yield : 22.4 g. Melting point : > 250°C. 10 g of the dyestuff were dissolved in 100 ml of methylene chloride and 10 ml of methanol and to the obtained solution 10 g of sodium hydroxide dissolved in 20 ml of water were added. After agitating the mixture the liquid organic phase was separated and dried with anhydrous potassium carbonate. The solvent of the organic phase was distilled off and the solid residue left was boiled with ethanol.

Yield of colourless dye precursor compound : 7.7 g. Melting point : 177°C.

19. Preparation of dye precursor compound 19

6.7 g (0.033 mole) of 3-phenyl-propiolic aldehyde diethyl acetal dissolved in 50 ml of ethanol were added dropwise to 15 g (0.066 mole) of 2-p-methoxyphenylindole dissolved in a mixture of 75 ml of ethanol and 50 ml of ethanol saturated with hydrogen chloride gas.

After a reaction period of 2 hours the crystalline dyestuff was separated by suction and washed with a small amount of ethanol.

Yield : 18.2 g. Melting point : > 250°C.

5 g of the obtained dyestuff were dissolved in 100 ml of methylene chloride and allowed to react with 5 ml of morpholine. After evaporating the solvent the residue was washed with water.

Yield of the dye precursor compound : 5 g. Melting point : 135°C.

20. Preparation of dye precursor compound 20

To 6 g of the dyestuff prepared as described in preparation 1 and dissolved in 100 ml of methylene chloride 3 ml of morpholine were added. The solvent was evaporated and the residue washed with water and with methanol.

Yield of the dye precursor compound : 5.8 g. Melting point : 150°C.

21. Preparation of dye precursor compound 21

The preparation of said dye precursor compound proceeded analogously to the preparation of compound 16.

Melting point : 176°C.

22. Preparation of dye precursor compound 22

20.1 g of dyestuff prepared as starting compound for the preparation of dye precursor compound 21 were dissolved in a mixture of 150 ml of methylene chloride and 50 ml of methanol. To the obtained solution 11.9 ml of triethanolamine were added dropwise.

The obtained reaction mixture was poured into water. The organic phase was separated and dried with anhydrous potassium carbonate. After evaporating the solvent the dye precursor compound was recrystallized from a mixture of methanol and isopropanol (1:1 by volume).

Yield : 8.5 g. Melting point : 125°C.

23. Preparation of dye precursor compound 23

12.24 g (0.06 mole) of 3-phenyl-propiolic aldehyde diethyl acetal dissolved in 50 ml of ethanol were added dropwise to 25 g (0.12 mole) of 1-methyl-2-phenylindole dissolved in a mixture of 75 ml of ethanol and 25 ml of ethanol saturated with hydrogen chloride gas. The reaction mixture was cooled down to 0°C, whereupon the dyestuff crystallized.

Yield : 24.2 g. Melting point : 235°C.

6 g of dyestuff were dissolved in 100 ml of methylene chloride and allowed to react with 6 ml of morpholine. The solvent was evaporated and the residue washed with water and methanol.

Yield of colourless dye precursor compound : 5.9 g. Melting point : 198°C.

24. Preparation of dye precursor compound 24

4.15 g (0.01 mole) of 1,2,3,3-tetramethyl-5-difluoromethylsulfonylindoleninium iodide and 2.7 g (0.01 mole) of 1-methyl-2-p-chlorophenyl-3-formylindole were boiled for 10 min. in 30 ml of acetic anhydride. The dyestuff crystallized.

Recrystallization of the dyestuff precipitate was effected with a mixture of acetone and methanol (1:1 by volume).

Yield of the dyestuff : 3 g. Melting point : > 250°C.

To a solution of 5 g of dyestuff in 100 ml of methylene chloride 10 ml of morpholine were added. The mixture was washed with water and the organic phase dried with potassium carbonate. After evaporating the solvent 4.5 g of dye precursor compound were obtained.

Melting point : 150°C.

25. Preparation of dye precursor compound 25

5 g of dyestuff prepared as described in preparation 24 were dissolved in 100 ml of methylene chloride and treated with 30 ml of an aqueous 5 n sodium hydroxide solution. The organic phase was dried with anhydrous potassium carbonate and thereupon the solvent distilled off.

Yield of dye precursor compound : 3 g. Melting point : 210°C.

26. Preparation of dye precursor compound 26

A solution of 27.1 g (0.1 mole) of 1-p-carbethoxyphenyl-2,5-dimethyl-4-formyl-pyrrole in 200 ml of ethanol were dropwise added to a mixture of 24.3 g (0.1 mole) of 1-p-carbethoxyphenyl-2,5-dimethylpyrrole and 20 ml of perchloric acid (70% aqueous solution) dissolved in 160 ml of ethanol. During the addition the temperature of the reaction mixture was kept at 10°C. The crystallized dyestuff was separated and washed with ethanol and ether.

Yield : 52 g. Melting point : 218°–223°C.

19.6 g of dyestuff were dissolved in a mixture of 120 ml of methylene chloride and 40 ml of methanol and 9 ml of triethylamine added thereto. The obtained colourless solution was poured into water. The organic phase was dried with anhydrous sodium carbonate and the solvent evaporated.

Yield : 16 g. Melting point : 100°C (decomposition).

27. Preparation of dye precursor compound 27

To 19.7 g of dyestuff prepared as described in preparation 26 and dissolved in 150 ml of methylene chloride 5.8 ml of morpholine were added dropwise. The colourless solution was poured into water. After separating the organic phase and drying it with anhydrous sodium carbonate the solvent was evaporated.

Yield : 16 g. Melting point : 100°C (decomposition)

28. Preparation of dye precursor compound 28

The dye precursor compound has been prepared analogously to preparation 16.

Melting point : 154°C.

29. Preparation of dye precursor compound 29

To 6 g of dyestuff prepared as described in preparation 23 and dissolved in a mixture of 80 ml of methylene chloride and 20 ml of methanol 6 ml of triethylamine were added. The reaction mixture was poured into water. The organic phase was dried with anhydrous sodium carbonate and the solvent evaporated. The residue was washed with methanol.

Yield of dye precursor compound : 4.3 g. Melting point : 140°C.

30. Preparation of dye precursor compound 30

While keeping the temperature of the reaction mass at 10°C a solution of 30 g (0.11 mole) of 1-(p-carbethoxy-phenyl) 2.5-dimethyl-3-formylpyrrole in 100 ml of ethanol were added dropwise to a solution of a mixture of 20.4 g (0.11 mole) of 1-)p-tolyl)-2,5-dimethylpyrrole and 22 ml of a 70% aqueous solution of perchloric acid dissolved in 160 ml of ethanol. The crystallized dyestuff was separated and washed with diethylether.

Yield : 51 g. Melting point : 150°–155°C (decomposition).

To a solution of 16.1 g of the dyestuff dissolved in 120 ml of methylene chloride 5.2 ml of morpholine were added dropwise. The obtained colourless solution was poured into water. The organic phase was dried with anhydrous sodium carbonate and the solvent removed. The residue was digested with methanol.

Yield of dye precursor compound : 6.3 g. Melting point : 135°C.

31. Preparation of dye precursor compound 31

To 16.1 g of dyestuff prepared as described in preparation 30 and dissolved in 120 ml of methylene chloride 5.9 g of piperidine were added dropwise. The obtained colourless solution was poured in water. The organic phase was separated and dried with anhydrous sodium carbonate and the solvent evaporated. The residue was digested with methanol.

Yield of dye precursor compound : 7 g. Melting point : 120°C.

The aromatic and heterocyclic aldehydes used in the above described preparations have been prepared by the Vilsmeyer reaction which reaction has been described e.g. by Donald J. Cram and George S. Hammond in Organic Synthesis - 2nd Edition (1964) Mc Graw-Hill Book Company Ind. New York - pp. 446-447 and by Houben-Weyl in Methoden der Organische Chemie Bd. III, Teil 1, p. 30.

As an example of the synthesis of said aldehydes the following preparation is given in detail.

Preparation of 1-methyl-2-phenyl-3-formyl-indole

To 150 ml of dimethylformamide 46 ml of phosphorus oxychloride were added dropwise care being taken that the temperature of the reaction mixture did not rise above 20°C. Subsequently to the obtained mixture 103.5 g of 1-methyl-2-phenylindole dissolved in 200 ml of dimethylformamide were added dropwise. During the addition the reaction mixture was kept at a temperature in the range of 20° to 40°C and thereupon for 1 hour kept between 40° and 45°C. Then the reaction mixture was poured into a solution of 490 g of sodium acetate dissolved in 500 ml of water to which 500 g of ice were added. The precipitated aldehyde was separated by suction, washed with water and methanol.

Yield : 105 g. Melting point : 125°C.

Starting products such as 2,5-dimethylpyrrole derivatives have been prepared analogously to the synthesis of 2,5-dimethylpyrrole described in Org. Synth. Coll. Vol. II, 219.

The synthesis of 2-morpholino-3,4-diphenyl-thiophene has been described by H. Hartmann and R. Mayer, Z. Chem. 6, 28 (1966).

The synthesis of the indole derivatives has been carried out analogously to the synthesis of 2-phenyl-indole as described by W.E. Noland et al., J. Org. Chem. 31, 65–69 (1966).

The synthesis of 2,3-diphenylindolizine has been carried out analogously to the synthesis of substituted indolizines described e.g. in the United Kingdom Patents 658,560 filed Apr. 1, 1949 and 999,874 filed July 21, 1960 both by Kodak Ltd.

The reaction of acid with the above dye precursor compounds results in the production of methine dyes probably having a resonance system of the type as illustrated in the following compound:

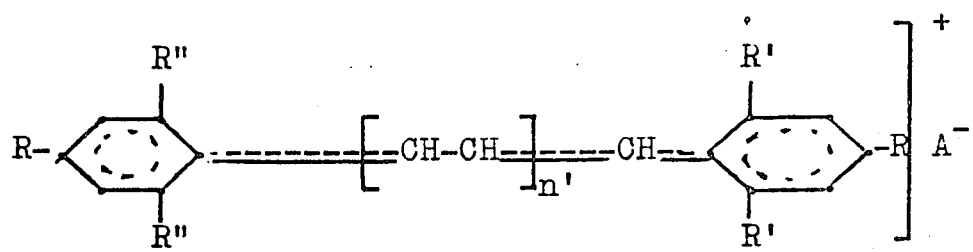

wherein:

R, R', and R'' are methoxy groups, n' is 0, 1, or 2, and

A⁻ is an anion (see Angew. Chem./73 Jahrg. 1961/Nr. 13, page 467).

As proton-donating reagent any acid or compound reacting as an acid can be used. The acid is used in encapsulated or enveloped state or it is provided in a separate rupturable layer.

According to a preferred embodiment acid solid particles e.g. acid-activated siliceous compounds are used that are dispersed in a hydrophilic binder. Suitable siliceous compounds are e.g. attapulgite, montmorillonite, clay, and bentonite. Usually these compounds are inappropriate for use as sizings or substitutes for paper pulp. They are used as pigments in coatings applied to a support e.g. a paper sheet. Acid compounds that may be used for entering into reaction with the present dye precursor compounds are preferably solid acids e.g. benzoic acid, succinic acid, citric acid, cyanoacetic acid, oxalic acid, salicylic acid, 5-bromosalicylic acid, a sulfamic acid (i.e. an organic acid of the type $(R'_1.R'_2)$—N—SO$_2$OH in which $R'_1$ and $R'_2$ are organic groups), p-tolusulfonic acid, maleic acid, 2,4-dichloromaleic acid, phthalic acid, and the anhydrides of these acids. In general, acids having a pKa value between 2 and 5 are effective.

Examples of salts that react as an acid are e.g. monosodium citrate, potassium aluminium sulfate, aluminium sulfate, potassium hydrogen tartrate, sodium hydrogen phosphate, ammonium gallate, ammonium benzoate, and dichlorobenzidine dihydrochloride.

Examples of solid prototropic compounds that are useful for the dye formation according to the present invention are saccharine, barbituric acid, and uric acid. These compounds are not proton-donating at room temperature so that premature colour formation therewith is avoided. In heating conditions above 60°C they become actively proton-donating.

In order to prevent premature colour formation at least one of the reactants is shielded from the necessary co-reactant by means of a pressure-rupturable material, which in normal pressure conditions prevents the colour reaction.

According to one embodiment one of the reactants is encapsulated separately in pressure-sensitive envelopes preventing the colour reaction in normal pressure conditions.

In principle all techniques known in the art for encapsulating solids or liquids can be used for the purpose of the present invention. Three types of encapsulating techniques can be considered depending on the type of material to be encapsulated:

A. encapsulation of an aqueous phase,
B. encapsulation of an organic lipophilic phase, and
C. encapsulation of finely divided solid substances.

Since the colour reaction applied according to the present invention proceeds very quickly in a liquid medium, which is a solvent for hydrogen ions and/or the compounds producing such ions, some water and/or other liquid, e.g. glycerol, allowing the existence of said ions in free state may be incorporated into the recording material so that said liquid stands in contact with at least one of the reactants or by the rupture of the pressure-sensitive shielding material can come into contact with all the reactants.

Thus, according to a particular embodiment some water is encapsulated together with at least one of the reactants. In order to prevent or retard the removal of water from the recording material by evaporation on storage (a) hygroscopic compound(s) or water-retaining compounds are used e.g. 1,2-dihydroxyethane, glycerol, (an) aqueous gel-forming compound(s), e.g. pectine, or (a) hygroscopic salt(s), e.g. magnesium chloride, and (a) compound(s) with a substantial amount of crystal water, e.g. sodium tetraborate-10-water.

Suitable techniques for the encapsulation of water or an aqueous phase have been described in the United Kingdom Patents 898,668 filed Feb. 27, 1961, by IBM, 929,403 filed Nov. 9, 1959 and 929,470 filed Nov. 26, 1959 both by Upgohn C$_o$, 1,048,696 and 1,048,697 both filed July 10, 1963 by Gevaert Photo-Production N.V. One of the reactants may be encapsulated in a liquid organic phase or as a solid particle.

For details about the encapsulation in an organic phase reference is made to the United Kingdom Patents 1,042,596, 1,048,697 as mentioned above, the U.S. Pat. 2,712,507 of Barrett K. Green issued July 5, 1955, the Canadian Patent 636,970 filed Apr. 13, 1959 by National Cash Register, and the French Patents 1,304,891 filed Oct. 31, 1961 and 1,312,868 filed Jan. 29, 1962 both by IBM. For details about the solid phase encapsulation reference is made to the United Kingdom Patent 920,866 filed Aug. 15, 1961 by National Cash Register C$_o$, the published Dutch Patent Application 6611661 filed Aug. 18, 1965 by National Cash Register C$_o$, and the Canadian Patent 627,609 filed Apr. 17, 1957 by Marco Inc.

According to one embodiment a pressure-sensitive sheet is formed by including microscopically small pressure-rupturable capsules, preferably not exceeding 50 microns and containing one of the reactive components, into a paper-forming slurry or wet stock of any paper-forming fibres, from which a web of unified fibres is manufactured.

The capsules are mixed thoroughly into the slurry or paper stock before application of the slurry to the paper-making machine. By a proper selection of capsule shell material, the capsules remain unruptured and readily retained in the wet slurry when the latter is deposited on a paper wire for forming a unified web and become an integral part of the web without requiring any binder in addition to the paper-forming pulp itself.

In a pressure-activatable single-sheet image-forming sheet at least one of the co-reactants for the reactants contained in the capsules is included in the sheet material in such a manner that they are adjacent to the capsules or stand in such relationship to each other that they can reach each other by diffusion, so that upon release by pressure of one of the reactants from the capsules a reaction takes place to provide a coloured mark in correspondence with the pressure applied.

According to a particular embodiment of the present invention a manifold paper system is built up. The CB-paper of said system is coated on its rear side with a pressure-transferable composition e.g. essentially comprising a frangible hydrophilic colloid layer or pressure-adhesive layer containing the acid compound or acid compounds (1) or dye precursor compound (2) or mixture of dye precursor compounds, whereas the front side of the CFB-paper is coated with a capsule layer, which is made to adhere thereto. Of course, the capsules contain the proper co-reactant for the reactant of the CB-paper. The CF-paper contains on its front side the same encapsulated reactant(s) as the front side of the CFB-paper. The CFB-paper contains on its rear side the same transferable reactant as the rear side of the CB-paper.

The encapsulation of aqueous compositions or water proceeds very advantageously according to the encapsulating technique described in the United Kingdom Patent Nr. 1,048,696 and Belgian Patent 792,550 as mentioned above. The encapsulating material preferably consists of a hydrophobic polymer that forms a water-insoluble capsule shell. Polymers suited for use according to the invention are, e.g., addition polymers formed by polymerisation or copolymerisation of vinyl monomers such as styrene, vinyl chloride, vinylidene chloride, vinyl alcohol esters e.g. vinyl acetate, vinyl ethers, acrylic acid esters and methacrylic acid esters, acrylonitrile and methacrylonitrile, and other $\alpha,\beta$-unsaturated monomers forming water-insoluble polymers. Other suitable polymers are condensation polymers such as water-insoluble polyesters, polyamides, and polyester-amides, e.g. polycarbonate, polycarboxylic acid esters of aliphatic diols and/or bisphenols, alkyd resins, polysulphonates, polyphosphonates and polyamide compounds derived from aliphatic amines. Further suitable polymers are addition polymers such as polyurethanes and chemically modified, e.g. hydrophobized, natural polymers e.g. chlorinated natural rubber and etherified cellulose, e.g. ethylcellulose.

According to the process described in the United Kingdom Patent Nr. 1,048,696 as mentioned above microcapsules comprising water, another aqueous material, or (a) hydrophilic substance(s) in a solid mantle of polymeric material are formed by:

a. emulsifying or dispersing the aqueous material or hydrophilic substance(s) in a solution of a polymeric material, the solvent for the latter being a water-immiscible organic solvent having a boiling point lower than 100°C, b. emulsifying the emulsion or dispersion obtained in an aqueous solution of a hydrophilic colloid, and (c) removing the solvent for the polymeric material by evaporation.

According to the Belgian Patent 792,550 as mentioned above microcapsules comprising an aqueous liquid in a hydrophobic envelope are prepared by a process involving the following steps:

A. emulsifying a volume $V_1$ of said aqueous liquid in a volume $V_2$ of a hydrophobic liquid consisting of or containing a substance or substances for forming hydrophobic capsule envelopes, the volume $V_1$ being such that the $$\frac{V_1}{V_1 + V_2}$$

ratio does not exceed that which corresponds with the first inversion point of the formed emulsion, and B. rapidly adding to such formed emulsion, while agitating or stirring, a volume $V_3$ of aqueous liquid to form an emulsion system comprising an aqueous liquid continuous phase and a disperse phase comprising droplets of aqueous liquid enveloped in a hydrophobic liquid phase consisting of or containing said envelope-forming substance(s), the volume $V_3$ being such that the $$\frac{V_2 + V_3}{V_1 + V_3 + V_2}$$

ratio is a little less than or is equal to or higher than that which corresponds with the second inversion point of the emulsion system and C. allowing or causing the said envelope-forming substance(s) in said enveloping hydrophobic liquid phase to form solid envelopes around said droplets.

The thickness and the rupturability of the capsule shell can be controlled by adjusting the volume ratio between the liquid phase to be encapsulated and the hydrophobic (water-immiscible) phase. The lower this ratio the thinner the capsule shells will be.

Substances that slow down the evaporation of the water i.e. the drying out of the capsules are preferably applied in the capsule fill in a rather high concentration in respect of the water, e.g. 25% by weight. Examples of such substances include hygroscopic salts, e.g. magnesium chloride, glycerol, glycol, and sorbitol, and also hydrophilic colloids, e.g. gum arabic, carboxymethylcellulose, pectine, caseine, poly(vinyl alcohol), and poly-N-vinyl-pyrrolidone. Other substances are silicates, colloidal silica, and silicic acid.

However, the present pressure-sensitive materials do not necessarily contain microcapsules. For example, pressure-sensitive sheet materials are also prepared with good results according to a method comprising the steps of (1) dispersing oil droplets containing a colour-forming reactant e.g. the dye precursor compound in an aqueous solution of a precipitable hydrophilic colloid such as carboxymethylcellulose, (2) adding a precipitating agent to said solution, e.g. aluminium nitrate in the case of carboxymethylcellulose, while agitating the solution to cause precipitation of the carboxymethylcellulose with the oil-dye precursor compound droplets entrained therein, (3) coating the obtained mixture on a backing sheet and drying the coating. For such technique reference is made to the United Kingdom Patent 1,280,769 filed Mar. 24, 1970 by Machuwa $C_o$ which should be read in conjunction herewith.

According to an embodiment the conversion of the dye compound into the leuco dye compound proceeds during the mixing step of ingredients of the coating composition.

This procedure is much more economical than the procedure involving a separate conversion of the dye outside the coating composition and is completely reproducible.

The process is based on the fact that the dye compounds corresponding with the leuco dye compounds are easily converted at room temperature into the leuco form by adding an equivalent amount of a base.

So, according to that embodiment in the manufacture of a pressure-sensitive recording material the leuco-compound is prepared in the mixing device in which the coating composition is prepared by allowing to react the dye with a base before the introduction of the precipitating agent viz. the aluminium nitrate.

By the addition of the base(s), which preferably proceeds in a chemically equivalent amount with respect to the dye(s) or in a small excess so that e.g. a pH of 8 is obtained, the coating composition decolourizes.

The alkaline substance or base, which is used to transform the dye in its leuco form, is e.g. an inorganic base such as sodium hydroxide, ammonium hydroxide or an organic amine e.g. an aliphatic, alicyclic or heterocyclic amine or "onium" hydroxide compound derived therefrom, or hydrazine, hydrazine hydrate or organic hydrazine. Preferably one of the following amines is used in the conversion of the dye into its leuco form : n-butylamine, ethanolamine, diethanolamine, triethanolamine, cyclohexylamine, dicyclohexylamine, dimethylenetriamine, (H₂N—CH₂—NH—CH₂—NH₂), urotropine, piperidine or morpholine. The alkaline substances may be applied from a solution in water or a mixture of water and a water-miscible organic solvent.

Thus prepared coatings are suited for use in multiple-sheet pressure-sensitive sheet systems (manifold pack) in which an acid-sensitive dye precursor compound is used in a coating on the rear side of a first sheet that stands in pressure-activatable reactive contact with an acid compound e.g. acidified white clay particles applied in a coating on the front side of a second sheet. Writing pressure effected on the uncoated side of the first sheet produces a dye image at the clay-coated side of the second sheet, the dye image having the colour determined by the colour precursor compound or mixture of colour precursor compounds used.

Pressure-sensitive recording materials of the present invention can be used in a method of making hectographic copies from a receiving sheet called here "printing master sheet" onto which the dye precursor compound is transferred by image-wise pressure from a rupturable or frangible coating to a transfer sheet.

Prior to the printing the dye precursor compound is converted into the corresponding methine dye salt, which is soluble in alcohol and/or water. Duplicating takes place from the printing master by moistening copy sheets to be printed by means of a neutral reacting copying liquid forming a solvent for the dye salt.

The rupturable coating of the transfer sheet can be used also to prepare the hectographic printing master in a photomechanical way e.g. along the steps of the process described in the U.S. Pats. 3,159,484 of Albert Amiel Van Hoof and 3,159,485 of Albert Emiel Van Hoof and Georges Arthur Holvoet both issued Dec. 1, 1964.

The following examples illustrate the present invention without, however, limiting it thereto. The percentages and ratios are by weight unless otherwise indicated.

EXAMPLE 1

Preparation of a pressure-sensitive sheet containing a dye precursor compound according to the general formula.

In the preparation of such sheet 3 solutions were used.

Solution A

| | |
|---|---|
| 10 % aqueous solution of carboxymethylcellulose (Hercules (registered trade mark) CMC-7L) | 75 g |
| 35 % aqueous solution of urea-formaldehyde resin (Beetle resin BC 32 of British Imperial Products) | 5.3 g |
| water | 111.5 g |

Solution B

| | |
|---|---|
| chlorinated diphenyl (Aroclor (registered trade mark) 1242 | 19.8 g |
| isooctyl-isodecyl phthalate (Santicizer (registered trade mark 602) | 3.3 g |
| a dye precursor compound or mixture of such compounds according to the present general formula | 0.9 g |

Solution C

| | |
|---|---|
| 2.06 % aqueous aluminium nitrate solution | 15.8 g |

Solution A was first formed by combining the carboxymethylcellulose solution and the urea-formaldehyde resin in the indicated amount of water with stirring until uniform dissolution (10 min.). With further stirring at low speed in a WARING BLENDOR (trade name of a mixing apparatus) solution B was added slowly and stirring was continued for 10 min. Thereupon solution C was added dropwise in 10 min. at high speed stirring and the high speed stirring was continued for an additional period of 10 min.

The composition obtained was coated with a knife coater on a paper base at a wet thickness of 0.002 inch The coating was dried. The resulting pressure-sensitive recording sheet was suited for use as CB-paper in a manifold pack. The front of an adjacent CF-paper was coated with a coating composition formed as follows:

| | |
|---|---|
| water | 53 g |
| 5 % aqueous solution of tetrasodium pyrophosphate | 2 g |
| 10 % aqueous solution of oxalic acid | 5 g |
| 20 % aqueous solution of polyvinyl alcohol (Gelvatol (registered trade mark) 20–30) | 20 g |
| acid-activated montmorillonite clay | 20 g |

This composition was coated at a ratio of 60 to 80 g of solids per sq. m.

With the dye precursor compounds identified by number in the mentioned Table in the CB-paper the following colours were obtained on pressure recording (e.g. type-writing on the manifold pack) in the front coating of the CF-paper containing the acidified clay.

| Number of dye precursor compound | Colour |
|---|---|
| 1 | magenta |
| 2 | magenta |
| 11 | magenta |
| 18 | greenish yellow |
| 8 | magenta |
| 9 | orange |
| 29 | cyan |
| 23 | cyan |
| 32 | orange |
| 33 | orange |
| 34 | greenish cyan |
| 35 | greenish cyan |
| 9 + 34 | black |
| 9 + 35 | black |
| 33 + 34 | black |
| 33 + 35 | black |

Preparation of dye precursor compound 39 corresponding to the following structural formula:

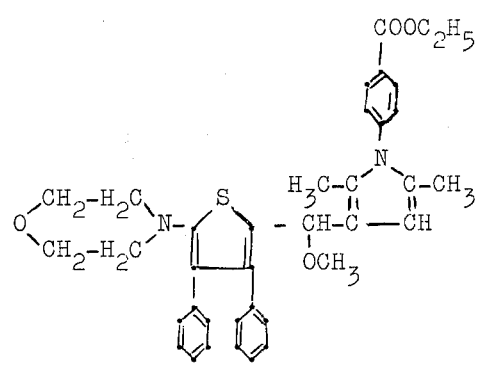

9.6 g (0.03 mole) of 2-morpholino-3,4-diphenylthiophene was dispersed in 50 ml of ethanol saturated with hydrogen chloride. 8.1 g (0.03 mole) of 1-p-carbethoxyphenyl-2,5-dimethyl-3-formylpyrrole dissolved in 7.5 ml of ethanol were added dropwise with thorough stirring. During the addition the reaction temperature was kept at a temperature of 15°. After a reaction period of 2 hours a solution of 10 g of sodium perchlorate in 20 ml of water was added. The crystallized dyestuff was separated and washed with water.

Yield: 16.6 g. Melting point: 200°–210°C.

10 g of the dyestuff obtained were dissolved in 100 ml of methylene chloride and 10 ml of methanol and then converted into the colourless leuco form by mixing it with 10 ml of aqueous ammonia. After drying of the organic phase with anhydrous potassium carbonate the solvent was evaporated and the leuco base recrystallized from butylacetate.

Yield: 4.7 g. Melting point: 234°C.

Preparation of dye precursor compound 40 corresponding to the following structural formula:

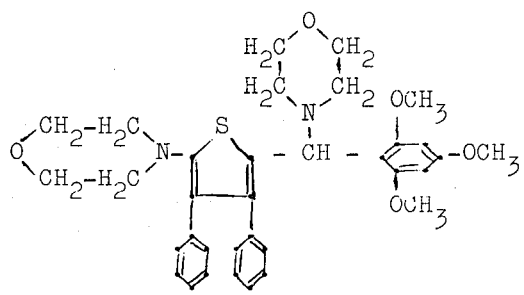

6 g of the dyestuff prepared as described in preparation 9 were dissolved in 100 ml of methylene chloride and allowed to react with 10 ml of morpholine. After washing with water and drying with potassium carbonate the solvent was evaporated. The residue was washed with water and dried.

Yield: 5.3 g. Melting point: 104°C.

Preparation of dye precursor compound 41 corresponding to the following structural formula:

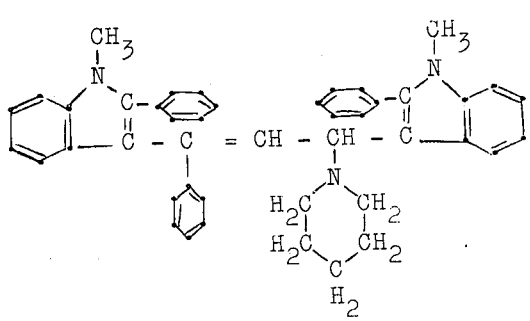

5.6 g of the dyestuff prepared as described in preparation 23 were dispersed in 100 ml of methyl ethyl ketone and allowed to react with 2.5 ml of piperidine. After filtration of the crystalline precipitate of piperidine chlorohyd the solution was evaporated and the residue was washed with water and methanol.

Yield: 5 g. Melting point: 110°C.

Preparation of dye precursor compound 42 corresponding to the following structural formula:

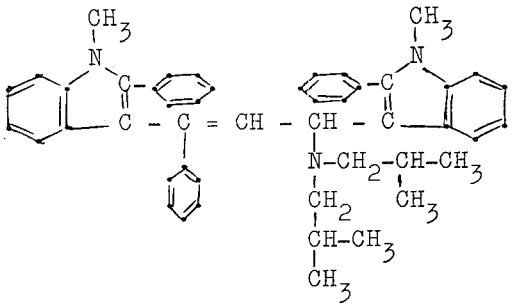

5.6 g of the dyestuff prepared as described in preparation 23 were dispersed in 100 ml of methyl ethyl ketone and allowed to react with 10 ml of diisobutylamine. After filtration of the crystalline precipitate of diisobutylamine chlorohydrate, the solution was evaporated and the residue washed with water.

Yield: 4.5 g. Melting point: 70°C.

EXAMPLE 2

Example 1 was repeated but with the following composition for the front coating of the CF-paper:

| | |
|---|---|
| 5 % solution of ethylcellulose in acetone | 100 g |
| p-tolusulphonic acid | 2 g |
| polyethyleneoxide (average molecular weight 400) | 2 g |
| wet coating thickness : 0.002 inch | |

Very sharp pressure prints are obtained by using this CF-paper. Equally good results are obtained by replacing p-tolusulphonic acid by a same amount of salicylic acid.

EXAMPLE 3

A solution A was formed at first by a 2 minutes mixing in a WARING BLENDOR (trade name of a mixing apparatus) at low stirring speed of the following ingredients:

| | |
|---|---|
| carboxymethylcellulose (CMC-70 Low Hercules Cellulose Gum of The Hercules Powder Company, Wilmington, Del., U.S.A.) | 7.5 g |
| urea-formaldehyde resin (Beetle resin BC 32 of British Imperail Products) | 1.9 g |
| water | 180 ml |

With further stirring at low speed a solution B was added and mixing was continued for 2 min.:

| | |
|---|---|
| tetrachlorobiphenyl | 19.8 g |
| iso-octyldecyl phthalate 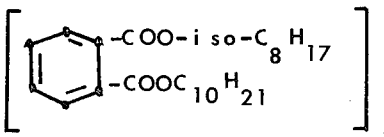 | 3.3 g |

Then the dyestuff having the following general formula:

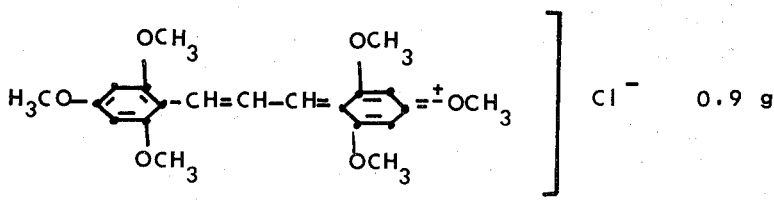

was added to the obtained solution and stirring was continued at high speed for 5 min.

Thereupon 0.2 g of morpholine was added which resulted in the decolourization of the mixture and the conversion of the dyestuff to the corresponding leuco form. Mixing was continued at low speed for 5 min. and a 2% aqueous solution of aluminium (III) nitrate was added in an amount sufficient to reach a pH of 7.0.

The obtained dispersion was knife-coated on a paper base having at its surface a pH of 6.0, the wet coating thickness being 0.002 inch.

The coating was dried. The resulting pressure-sensitive recording sheet was suited for use as CB-paper in a pressure-sensitive manifold paper pack and yielded magenta pressure prints corresponding with the applied pressure markings.

The composition of a pressure-sensitive manifold paper pack is described in detail in the main patent, which should be read in conjunction herewith.

EXAMPLE 4

Example 3 was repeated with the difference, however, that instead of the mentioned dyestuff 0.65 g of a dyestuff corresponding with the following formula:

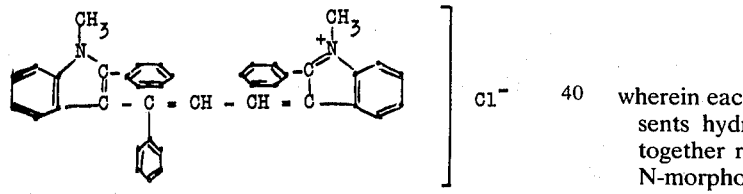

was used, and the morpholine was replaced by 0.2 g of n-butylamine. With the obtained material cyan pressure prints were produced.

EXAMPLE 5

Example 3 was repeated with the difference, however, that the magneta dyestuff was replaced by a mixture of the following dyestuffs:

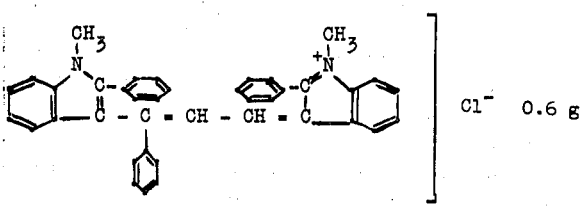

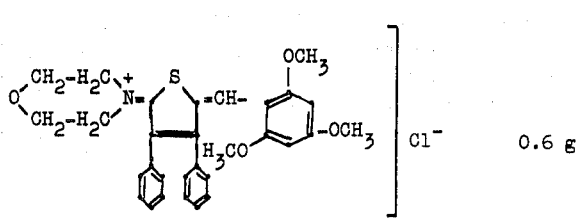

Grey, almost black pressure prints were obtained with a pressure-sensitive material containing said mixture of dyes.

We claim:

1. A pressure-recording process in which a methine dye is produced by bringing image-wise into reactive contact with the aid of pressure an acid compound having a pKa of about 2–5 with a dye precursor compound corresponding to the following general formula and capable of reacting with said acid compound to form a methine dye:

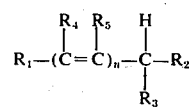

wherein:

$R_1$ represents an alkoxy substituted phenyl group, an indolyl group, a thienyl group, a carbazolyl group or a pyrrolyl group, $R_2$ represents an alkoxy substituted aryl group, an indolyl group, a thienyl group, a carbazolyl group or a pyrrolyl group, $R_3$ represents hydroxyl, alkoxy, or

wherein each of $R_8$ and $R_9$ (same or different) represents hydrogen or an alkyl group or $R_8$ and $R_9$ together represent the necessary atoms to close a N-morpholinyl nucleus or N-piperidyl nucleus, each of $R_4$ and $R_5$ represents hydrogen, or $R_4$ represents phenyl and $R_5$ hydrogen, and $n$ is 0 or 1.

2. A pressure recording process according to claim 1, wherein $R_1$ and/or $R_2$ represent a methoxysubstituted phenyl group.

3. A pressure recording process according to claim 1, wherein the thienyl group is substituted with a N-morpholinyl group.

4. A pressure-recording process according to claim 1, wherein the dye precursor compound and acid compound are present on separate support sheets and one of them is transferred by pressure from its support into reactive contact with the compound on the other sheet.

5. A pressure-recording process according to claim 1, wherein the dye precursor compound and acid compound are used in an integral copy-sheet containing on a same support the compound reacting as an acid out of direct chemical contact from the dye precursor compound but in such conditions that reactive contact can be effected through pressure.

6. A pressure-recording process according to claim 1, wherein at least one of the reactants is kept out of direct chemical contact from the other reactant by enveloping it in capsules or droplets from which the reactant is set free by pressure applied in an image.

7. A pressure-recoding process according to claim 1, wherein the dye precursor compound is applied to a support in a first hydrophilic binder layer and said first layer is coated with a second layer containing acid-treated clay in another hydrophilic binder shielding the acid clay from direct chemical contact with the dye precursor compound.

8. A pressure-recording process according to claim 1, wherein the material containing said dye precursor compound is present in a layer coated from a composition prepared by a method including the steps of:
1. dispersing oil droplets in an aqueous solution of a precipitable hydrophilic colloid,
2. adding a dyestuff that can be converted into the dye precursor compound,
3. adding a base to the obtained mixture in a sufficient amount to convert the dyestuff to the corresponding dye precursor compound, and
4. adding aluminum nitrate as precipitating agent to the obtained mixture in order to cause precipitation of the hydrophilic colloid.

9. A pressure-recording process according to claim 1, wherein the dye precursor compound and acid compound are present in a multiple-sheet pressure-sensitive recording material pack in which one reactant is contained in a coloring coating on the rear side of a first sheet that is writable on the front side and the corresponding co-reactant is provided in a receiving coating on the front side of a further sheet in contact with the rear side of the first sheet, said sheets being separatable from each other and containing the reactants in such condition that the contact of the sheets in the absence of pressure does not allow the formation of color.

10. A pressure-recording process according to claim 9, wherein the multiple sheet material is in the form of a manifold paper back in which the top sheet has said coloring coating at its rear side; at least one intermediate sheet has said receiving coating on its front side and said coloring coating at its rear side and the third sheet contains said receiving coating at the front side, but has no coating at its rear side.

11. A pressure-recording material being an integral copysheet containing on a same support an acid compound having a pKa of about 2–5 out of direct-chemical contact from a dye precursor compound but in such conditions that reactive contact can be effected through pressure, wherein said dye precursor compound corresponds to the following general formula:

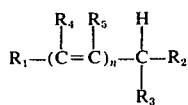

wherein:
R₁ represents an alkoxy substituted phenyl group, an indolyl group, a thienyl group, a carbazolyl group or a pyrrolyl group,
R₂ represents an alkoxy substituted aryl group, an indolyl group, a thienyl group, a carbazolyl group or a pyrrolyl group, R₃ represents hydroxyl, alkoxy, or

wherein each of R₈ and R₉ (same or different) represents hydrogen or an alkyl group or R₈ and R₉ together represent the necessary atoms to close a N-morpholinyl nucleus or N-piperidyl nucleus,
each of R₄ and R₅ represents hydrogen, or R₄ represents phenyl and R₅ hydrogen, and
n is 0 or 1.

12. A pressure-recording material according to claim 11, wherein R₁ and/or R₂ represent a methoxysubstituted phenyl group.

13. A pressure-recording material according to claim 11, wherein at least one of the reactants is kept out of direct chemical contact from the other reactant in capsules or droplets, from which it can be set free by pressure applied in the form of information.

14. A pressure-recording material according to claim 11, wherein the capsules or droplets are dispersed within the paper sheet itself or in a binder containing the second reactant in dispersed or dissolved form.

15. A pressure-recording material according to claim 11, wherein the acid compound is in solid particle form.

16. A pressure-recording material according to claim 15, wherein the solid acidic particles are distributed in an organic film-forming hydrophilic colloid substance insulating said particles from direct chemical contact with the dye precursor compound.

17. A pressure-recording material according to claim 11, wherein the dye precursor compound is applied to a support in a first hydrophilic binder layer and said first layer is coated with a second layer containing acid-treated clay in another hydrophilic binder shielding the acid clay from direct chemical contact with the dye precursor compound.

18. A pressure-recording material according to claim 11, being a multiple-sheet pressure-sensitive material in the form of a manifold paper pack in which the top sheet has said coloring coating at the rear side, at least one intermediate sheet has said receiving coating on its front side and said coloring coating at the rear side and the bottom sheet contains said receiving coating at the fron side, but has no coating on the rear side, wherein the coloring coating in said manifold paper pack contains said dye precursor compound and the receiving coating contains said acid compound.

19. A pressure-recording material according to claim 11, wherein said material is a multiple sheet pressure-sensitive recording material pack in which one reactant is contained in a coloring coating on the rear side of a first sheet that is writable on the front side and the corresponding co-reactant is provided in a receiving coating on the front side of a further sheet being in contact with the rear side of the first sheet, said sheets being separatable from each other and containing the reactants in such conditions that the contact of the sheets in the absence of pressure does not allow the formation of color.

* * * * *